United States Patent

Yamaguchi et al.

[11] Patent Number: 4,484,340
[45] Date of Patent: Nov. 20, 1984

[54] MULTICHANNEL CURRENT MEASURING APPARATUS FOR X-RAY COMPUTERIZED TOMOGRAPH

[75] Inventors: Keiki Yamaguchi; Tadashi Ogawa; Hideaki Uno, all of Tokyo, Japan

[73] Assignee: Yokogawa Hokushin Electric Corporation, Tokyo, Japan

[21] Appl. No.: 444,329

[22] Filed: Nov. 24, 1982

[30] Foreign Application Priority Data

Dec. 9, 1981 [JP] Japan ................................ 56-197912
Dec. 10, 1981 [JP] Japan ................................ 56-183783
Jul. 27, 1982 [JP] Japan ................................ 57-130742

[51] Int. Cl.$^3$ .............................................. A61B 6/02
[52] U.S. Cl. .................................................. 378/019
[58] Field of Search .......................... 378/19; 370/112; 250/385 R; 364/414

[56] References Cited

U.S. PATENT DOCUMENTS

4,134,018  1/1979  Weinkauf ............................ 378/019
4,152,543  5/1979  Prudhon et al. ..................... 370/112

Primary Examiner—Alfred E. Smith
Assistant Examiner—T. N. Grigsby
Attorney, Agent, or Firm—Moonray Kojima

[57] ABSTRACT

An apparatus for examining an input signal current from an X-ray detector in a computerized tomograph, wherein an apparatus is used to once charge a capacitor in each of a plurality of channels with the input signal current, and to read the charged voltage later to measure the strength of the respective input signals. To eliminate the effects of cross-talk, leakage current, and off-set factors, a reset switch alone or together with associated circuit elements are used. In one embodiment the reset switch is used to discharge distributed capacitance after reading of one channel capacitor and before the discharging of the next channel capacitor. In another embodiment the true input signal together with error factors are first measured and stored, and then the error factors are measured, and then such error factors are subtracted from the stored combined signal, to produce an output signal which reflects the true input signal. In another embodiment, the error factors are first measured, averaged and stored, and then the true input signal together with error factors are measured and stored, and then the two stored signals are retrieved and the error factor removed, thereby to produce an output signal which reflects the true input signal.

6 Claims, 6 Drawing Figures

MULTICHANNEL CURRENT MEASURING APPARATUS FOR X-RAY COMPUTERIZED TOMOGRAPH

BACKGROUND OF THE INVENTION

1. Field of the Invention

This invention relates to a multi-channel current measuring apparatus for applying a multichannel input signal current, obtained from an X-ray detector of an X-ray computerized tomograph, to each of a plurality of capacitors, and for reading the voltages of the capacitors, to examine the signal current in each channel.

2. Description of the Prior Art

An X-ray computerized tomograph is so constructed that an object to be examined is roetgenized and that the transmitted X-rays are detected by an X-ray detector, comprising a number of ionization chambers, to obtain projection data relating to the object based on signals provided by the detector. In this case, the tomograph is provided with a multichannel current measuring apparatus used to measure the strength of the output current of the ionization chamber in each of the multi-channels. To examine a number of ionization currents corresponding to the intensity of the transmitted X-rays thus obtained from the X-ray ionization chambers, a means may be used for applying each ionization current (hereinafter called input signal current) to a capacitor in each channel, once, and for measuring the strength of the charged voltage selectively at a subsequent time by the use of a sampling switch. However, disadvantageously, in such a method, simply using a sampling switch for reading the charged voltage of a capacitor may result in crosstalk, depending on distributed capacitance existing in the circuit.

In the multi-channel current measuring apparatus of the prior art, the ionization current, corresponding to the strength of the transmitted X-ray obtained from the X-ray ionization chamber, is converted into voltage on a per channel basis and digitalized by means of an analog-to-digital converter (AD converter). In this case, a leakage current may flow into the capacitor used for current/voltage conversion. In addition, because an amplifier for amplifying the charged voltage of a capacitor is not free from an off-set factor (also noise or other error factors) that cannot be ignored, it will be necessary to correct these error factors, if highly accurate measurement is required. Although the off-set factor of the amplifier may be corrected in an analog form through the so-called auto-zero method, no suitable correction means have been devised for reducing the error factors produced, for example, by the flow of leakage current in the circuit, into the capacitors.

SUMMARY OF THE INVENTION

Accordingly, an object of the invention is to overcome the foregoing and other deficiencies and disadvantages of the prior art.

Another object is to remove effects of cross talk caused by distributed capacitances in the circuit.

A further object is to eliminate the effects of leakage current, and off-set factors in the current measuring apparatus.

The foregoing and other objects of the invention are attained in an illustrative embodiment which encompasses an apparatus comprising a plurality of channels whereat a multichannel input signal currents from an X-ray detector are applied, a plurality of capacitors, each being associated with a respective channel, a plurality of sampling switches, each being associated with a respective channel, a reset switch connected common to all the channels and an amplifier having input and output means, the plurality of sampling switches being connected between the capacitors and the amplifier input. In other embodiments, there are circuit means for performing a variety of operations on the signals taken from the input signal as applied to the respective capacitors and transmitted via the respective closed sampling switches, to the amplifier.

In one embodiment, the reset switch is turned ON after the sampling switch of one channel is turned OFF so as to discharge any circuit distributed capacitance, thereby to eliminate cross talk between the channels from the distributed capacitance, and thereby produce an output which is accurately representative of the input signal from the X-ray detector.

In another embodiment, a combination of analog-to-digital converter, switching means, memory unit, operating means and timing control circuit, is employed to remove error factors, such as representing cross talk, leakage current and offset, from input signals supplied from the X-ray detector and operated on by the apparatus, and thereby produce an accurate reading of the input signal. In this embodiment, the aforementioned combination of elements act cooperatively together with the sampling switches and reset switch, first, to obtain a signal from each channel which comprises the true input signal and the error factors, and which is then digitalized and stored in the memory unit, and then, second, to obtain from each channel, error factors signals which are then together with the stored signals operated on by the operating means which subtracts out the error factors and transmits an output signal which represents the true input signal from the X-ray detector to each channel.

In a still further embodiment, a combination of analog-to-digital converter, two memory units, and two operating means, is employed, first, to obtain error factors of the circuit, without application of the input signals, which is then averaged over two cycles by one of the operating means, and stored in one of the memory units; and, second, to obtain a combined signal comprising the input signal and error factors, which combined signal is stored in the other memory unit, and then the stored combined signal and the stored averaged error factor signal, are retrieved by the other operating means and the averaged error factor signal is subtracted from the combined signal, thereby to produce an output signal which is representative of the true input signal from the X-ray detector to each channel.

A feature of the invention is the use of a reset switch to discharge distributed capacitance of one channel prior to reading the capacitance of the next channel.

Another feature is the switching of the reset switch for the period of time between the turning off of a sampling switch of one channel and the turning on of the sampling switch of the next channel.

A further feature is the combination of circuit elements to first obtain combination signals from each channel comprising input signal from an X-ray detector and error signal, and after amplification and conversion to digital form, storing the combination signal in a memory; and second, to obtain error signals from each channel without application of input signals from the X-ray detector, and after amplification and conversion to digital form, applying the error signals to an operating circuit for subtraction from the combined signal retrieved from the memory thereby to produce an output signal representative of the true input signal.

Another feature is the control of the timing of the obtaining of combined signals and of error signals so that the time of such obtaining after clearing of the capacitors, in each instance is substantially the same.

A yet further feature is a combination of circuit elements to first obtain error signals from each channel for at least two cycles, without application of input signals from an X-ray detector and after amplification and conversion to digital form, averaging the error signals and storing the averaged signal in a memory unit, and to second, obtain combination signals from each channel comprising input signals from the X-ray detector and error signals, and after amplification and conversion to digital form, storing the averaged error signal in a memory unit, and thereafter having the combined signal and averaged error signal applied to an operating circuit for subtraction of the error signal from the combined signal, thereby to produce an output signal representative of the true input signal.

DETAILED DESCRIPTION OF THE PREFERRED EMBODIMENTS

Figure 1:
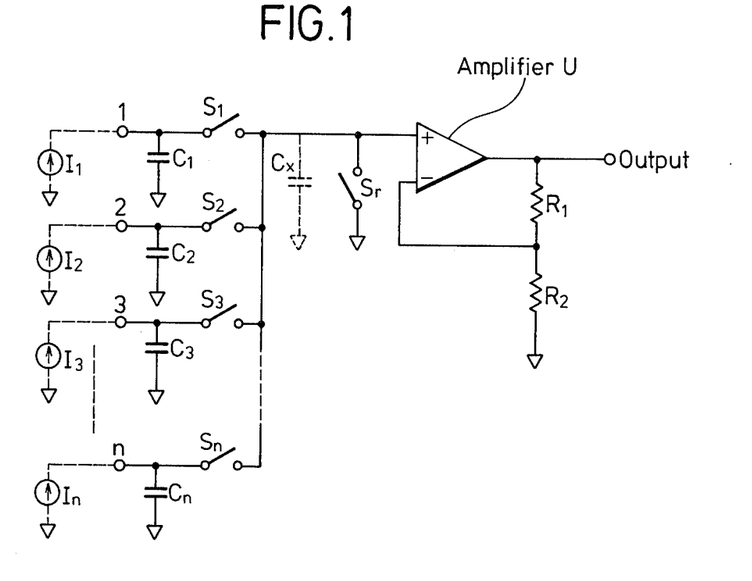
FIG. 1 depicts an illustrative embodiment of the invention.

Referring now more particularly to the drawing, FIG. 1 depicts the principal parts of an arrangement illustrating an example of a multi-channel current measuring apparatus for an X-ray computerized tomograph according to the present invention. In FIG. 1, designations $I_1-I_n$ are pulse input signal currents transmitted from an X-ray detector (not shown) for detecting an object (not shown) being examined. Capacitors $C_1-C_n$ are used for converting the input signal currents $I_1-I_n$ into voltages. Sampling switches $S_1-S_n$ are used to select the voltages of the capacitors $C_1-C_n$ and transmitting them to a next stage, that is to amplifier U. A multiplexer may be used in place of the switching elements $S_1-S_n$. The distributed capacitance which is produced in the input circuit of amplifier U, is designated by Cx. A reset switch Sr is shown connected to the input of the amplifier U and to the sampling switches $S_1-S_n$. The amplification factor of amplifier U is determined by resistors $R_1$ and $R_2$ connected to the amplifier U in the manner shown.

Capacitors $C_1-C_n$ are each connected between input channel terminals 1-n and circuit earth. Each of the input channel terminals 1-n is connected to amplifier U via a respective sampling switch $S_1-S_n$, and to circuit earth via the contact point of reset switch Sr.

Figure 2:
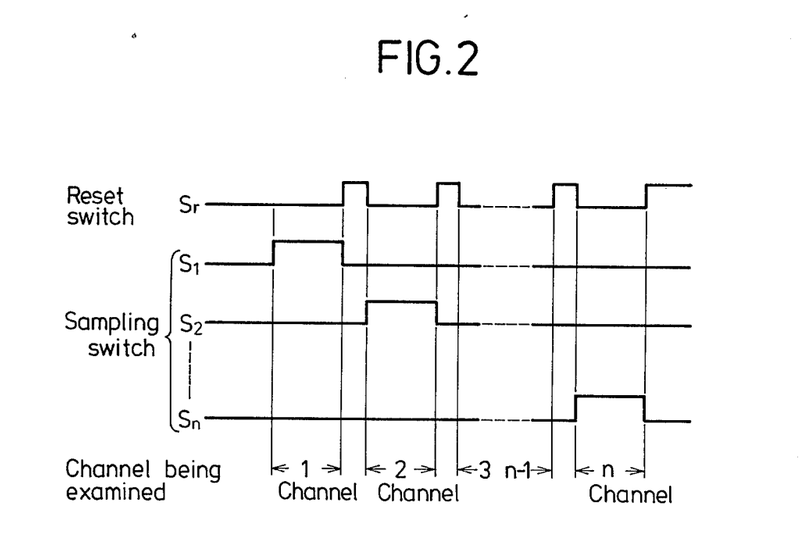
FIG. 2 is a time chart illustrating the operation of the embodiment of FIG. 1.

The description of the operation of the apparatus thus constructed as shown in FIG. 1 is given with reference to FIG. 2. FIG. 2 shows timing of sampling switches $S_1-S_n$ and of reset switch Sr. On the left side of each waveform, there is shown the designation of the switch corresponding to the waveform. Among the waveforms in FIG. 2, the switches are assumed to be in ON and OFF states when the waveforms are at a "high" and "low" levels, respectively.

The operation of FIG. 1 without use of the reset switch Sr is first described. Initially, all of the sampling switches $S_1-S_n$ are OFF, and the distributed capacitance Cx is assumed to be uncharged.

(A) Input pulse signal currents $I_1-I_n$ are applied to capacitors $C_1-C_n$ which are thus charged with voltages $E_1, E_2 \ldots E_n$.

(B) Next, only sampling switch $S_1$ is turned ON, and voltage $e_1$ given by the below equation (1) is introduced to amplifier U.

$$e_1 = \frac{C_1}{C_1 + C_x} \cdot E_1 \qquad (1)$$

Since the voltages of capacitors $C_1-C_n$ have been introduced to the non-turnover input terminal of amplifier U, it is not affected by input impedance.

(C) Voltage $e_1$ given by equation (1) is amplified suitably by amplifier U and the intensity of charged voltage $E_1$ of the capacitor $C_1$ is measured. In other words, the strength of the input pulse signal current $I_1$ applied to channel 1 is measured.

(D) Although sampling switch $S_1$ is subsequently turned OFF, voltage $e_1$ given by equation (1) remains in distributed capacitance Cx.

(E) When only sampling switch $S_2$ is turned ON, the voltage given by below equation (2) is supplied to input of amplifier U.

$$e_2 = \frac{C_2}{C_2 + C_x} \cdot E_2 + \frac{1}{C_2 + C_x} \cdot \frac{C_1 C_x}{C_1 + C_x} \cdot E_1 \qquad (2)$$

The value measured at this time, contains charged voltage $E_1$ of capacitor $C_1$ which causes cross talk. Given that the capacitance of capacitors $C_1-C_n$ is equal in value and that $C_x/C_1$ is about 1%, the value of about 1% of $E_1$ will be contained as cross talk, in measuring charged voltage $E_2$ of capacitor $C_2$. In the same way, error due to cross talk is included in the measured charged voltage of capacitors $C_3-C_4$ at all times.

Thus, without having and using the reset switch Sr of this invention, distributed capacitance Cx causes cross talk to occur, which is disadvantageous.

The operation of reset switch Sr, is as follows. Regarding step (A) hereinabove, operation is entirely the same. Subsequently, only sampling switch $S_1$ is turned ON and input signal current $I_1$ which is supplied to channel 1 according to the same operation described in steps (B) and (C) described above, is examined.

All the operation steps mentioned up to now, are the same as those described in steps (A)–(C), but the operation steps (D) and (E) are different. The reset switch Sr, is turned ON during the period of time after sampling switch $S_1$ is turned OFF and before sampling switch $S_2$ is turned ON, as shown in FIG. 2. Accordingly, the distributive capacitance Cx is discharged by the reset switch, and voltage $e_1$ shown in above equation (1) becomes zero for the next channel.

Since sampling switch $S_2$ is turned ON with distributed capacitance Cx not having been charged, voltage $e_2$ given by below equation (3) is applied to the input of amplifier U.

$$e_2 = \frac{C_2}{C_2 + C_x} \cdot E_2 \qquad (3)$$

In other words, the effect of voltage $E_1$ allowed to occur in equation (2) has been eliminated in the present invention and the strength of voltage $E_2$ based on the input signal current $I_2$ flowing in the object being examined, is accurately measured without any substantial cross talk.

According to the invention, no cross talk is produced because charge of distributed capacitance $C_x$, is discharged by turning ON reset switch Sr during the period after the voltage of a certain capacitor $C_k$ is measured, and before the voltage of the next capacitor $C_{k+1}$ is measured.

Although reset switch Sr in IF. 1 was turned ON during the entire period of time between the changeover of the sampling switches (e.g. $S_1$ to $S_2$), this invention is not limited to such a method. For example, reset switch Sr may be switched ON until charged stored in distributed capacitance $C_x$ is discharged and thereafter turned OFF.

In FIG. 1, reset switch Sr is connected to the non-turnover input terminal (e.g. positive terminal) of amplifier U, but the present invention can be practiced even if the switch is connected to a turnover input terminal (e.g. negative terminal).

Figure 3:
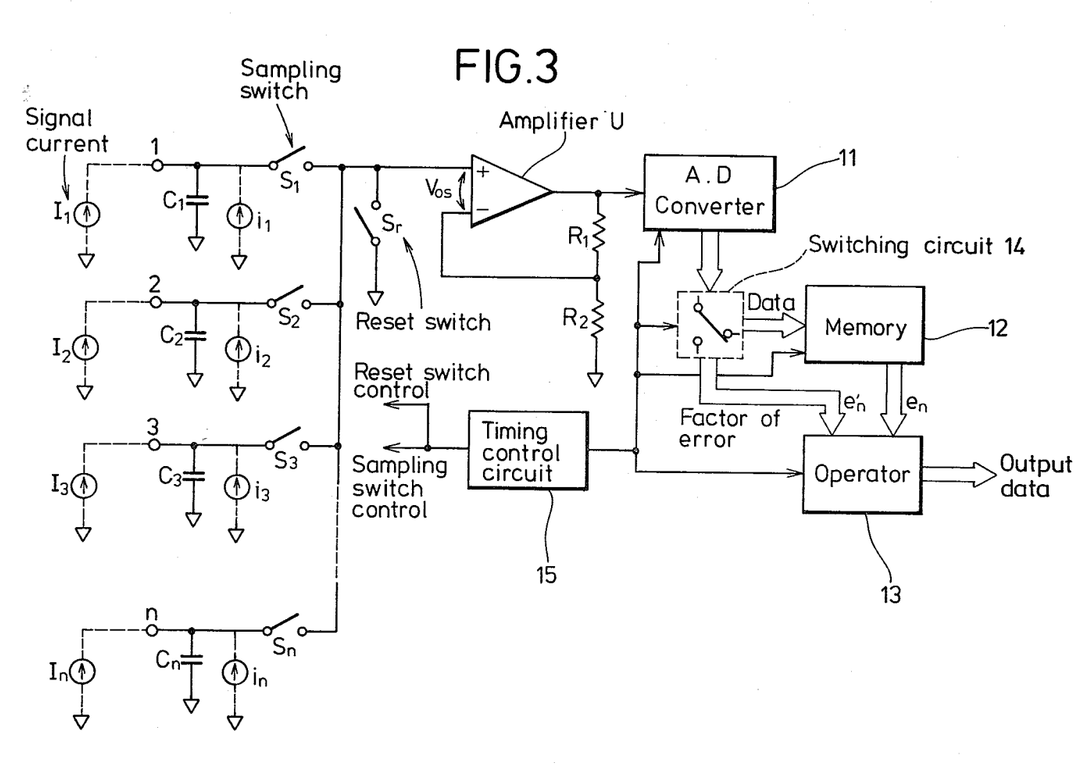
FIG. 3 depicts another illustrative embodiment of the invention.

FIG. 3 depicts principal parts of an arrangement of another example of a multichannel current measuring apparatus for an X-ray computerized tomograph according to the present invention. In FIG. 3, the description of input current signals $I_1$-$I_n$, and elements $C_1$-$C_n$, $S_1$-$S_n$, Sr and U is omitted since they are the same as those described in FIG. 1, and for sake of clarity of description. In addition to those items, there is depicted an analog-to-digital (AD) converter 11, used to convert and analog signal to a digital signal, a memory 12, for storing the output of AD converter 11, an operator 13 for suitably computing two digital signals, a switching circuit 14 for transmitting a signal from AD converter 11 to memory 12 and to operator 13, in a suitable manner, and a timing control cirucit 15 for controlling the timing of sampling switches $S_1$-$S_n$, reset switch Sr, AD converter 11, memory 12, switching circuit 14 and operator 13.

Capacitors $C_1$-$C_n$ are each connected between input channel terminals 1-n and circuit earth (i.e. ground). Each of input channel terminals 1-n are connected to amplifier U via each of sampling switches $S_1$-$S_n$, and then to the circuit earth via the contact point of reset switch Sr, as depicted. The output of amplifier U is applied to AD converter 11. The output of AD converter 11 is introduced into memory 12 or operating means 13 via switching circuit 14. As shown in FIG. 3, timing control circuit 15 is used to control the timing of each device. Currents $i_1$-$i_n$ which are added to the respective capacitors $C_1$-$C_n$ in parallel, represent leakage currents.

Figure 4:
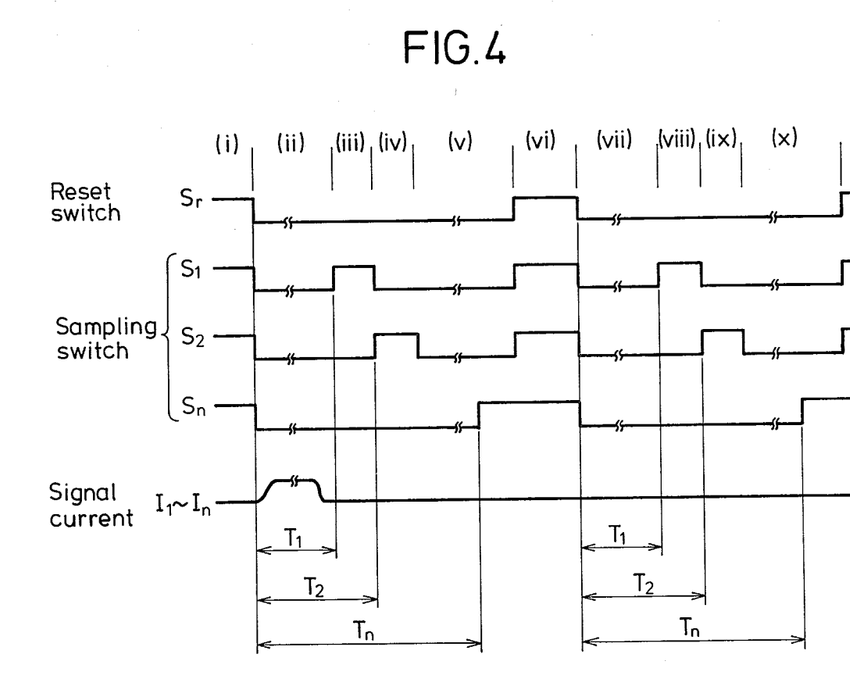
FIG. 4 is a time chart illustrating the operation of the embodiment of FIG. 3.

The operation of the arrangement of FIG. 3 is described hereinbelow with reference to FIG. 4. FIG. 4 is a diagram illustrating the timing of sampling switches $S_1$-$S_n$, reset switch Sr and input signal currents $I_1$-$I_n$. In FIG. 4, designations (i)-(x) show time periods. On the left side of each waveform, there are shown the name and signal current conforming to each waveform. The respective switch is assumed to be turned ON and OFF during the periods when the respective waveform is at a "high" and "low" level respectively.

There are preferably two conditions or stages of operation. First, the input signal and error factors are determined and, for example, stored in a memory; and then, second, the error factors are measured, without application of the input signal, and the error factor subtracted from the input signal having the error factor contained therein and previously stored, thereby to produce an output signal representative of the true or accurate input signal. Operation of the circuit of FIG. 3 during periods (i)-(x) is described below.

MEASUREMENT AND STORAGE OF COMBINED SIGNAL COMPRISING INPUT SIGNAL AND ERROR FACTORS

Period (i)

Reset switch Sr and sampling switches $S_1$-$S_n$ are turned ON and the charges in capacitors $C_1$-$C_n$ are discharged.

Period (ii)

Switches $S_1$-$S_n$ and Sr are turned OFF and capacitors $C_1$-$C_n$ are charged with input signal currents $I_1$-$I_n$ flowing in the respective channels. In addition, leakage current $i_1$-$i_n$ (representing, e.g. error factors) each flow inot capacitors $C_1$-$C_n$ as shown in FIG. 3. The direction in which the leakage currents flow is nop limited to that shown in FIG. 3. For example, the charges may flow out of capacitors $C_1$-$C_n$.

Period (iii)

As shown in FIG. 4, only sampling switch $S_1$ is turned ON at time $T_1$ after the charges in capacitors $C_1$-$C_n$ have been discharged by reset switch Sr. Accordingly, the charged voltage of capacitor $C_1$ is amplified by amplifier U, converted into a digital signal $e_1$ by AD converter 11, and then stored in memory 12 (see FIG. 3). At this time, output voltage $E_1$ of amplifier U is given by equation (4) set forth hereinbelow.

$$E_1 = \left\{ \frac{1}{C_1} \int_0^{T_1} (I_1 + i_1)dt + V_{os} \right\} G \qquad (4)$$

wherein $V_{os}$ is an off-set voltage of amplifier U and G is amplification degree of amplifier U. In other words, input current signal $I_1$, leakage current $i_1$ that has flowed into capacitor $C_1$ during time $T_1$ and voltage $E_1$ comprising an off-set voltage of amplifier U, are examined during period (iii). Then, voltage $E_1$ is converted by AD converter 11 into digital signal $e_1$ and stored in memory 12.

Periods (iv) and (v)

During these periods, each of input signal currents $I_2$-$I_n$ applied to channel 2-n, is examined by the same operation as that shown in period (iii). Referring to channel n, only sampling switch Sn is turned ON at time $T_n$ after capacitors $C_1$-$C_n$ have been discharged by reset switch Sr. Therefore, the charged voltage in capacitor $C_n$ is amplified by amplifier U, converted into a digial signal $e_n$ by AD converter 11 and then stored in memory 12. At this time, the output voltage $E_n$ of amplifier U is given by below equation (5).

$$E_n = \left\{ -\frac{1}{C_n} \int_0^{T_n} (I_n + i_n)dt + V_{os} \right\} G \quad (5)$$

Period (vi)

In the same way as that described in period (i), reset switch Sr and sampling switches $S_1$-$S_n$ are turned ON and the charges in capacitors $C_1$-$C_n$ are discharged.

MEASUREMENT OF ERROR FACTOR AND SUBTRACTING ERROR FACTOR FROM COMBINED SIGNAL TO PRODUCE OUTPUT SIGNAL

Period (vii)

The input signal current $I_1$-$I_n$ are not applied during time period (vii)-(x), as shown. The duration of period (vii), is the same as for period (ii), and is likewise labeled $T_1$. It is preferred that both time periods be the same. However, if the two periods are substantially the same, the object of the present invention can still be attained. As seen in FIG. 4, the other time periods $T_2 \ldots T_n$, are similarly considered.

Periods (viii) . . . (x).

Error factors based on leakage currents $i_1$-$i_n$ from channel 1 to channel n and off-set voltage $V_{os}$ of amplifier U are examined. Referring to channel n, the charged voltage after leakage current $i_n$ has flowed into capacitor $C_n$ over a period of time $T_n$ since the discharge of capacitor $i_n$, is examined. The output voltage $E_n'$ of amplifier U is shown by the below equation (6).

$$E_n' = \left\{ -\frac{1}{C_n} \int_0^{T_n} (i_n dt) + V_{os} \right\} G \quad (6)$$

As described above, the current signals including the error factors measured during periods (iii)-(v) are stored in memory 12 as digital signals $e_1$-$e_n$. On the other hand, during periods (viii)-(x), the error factor given by equation (6) is observed. The voltage $E_n'$ in equation (6) is converted into digital signal $e_n'$ by AD converter 111. Accordingly, two digital signals $e_1$ and $e_1'$; $e_2$ and $e_2'$; . . . $e_n$ and $e_n'$, corresponding to each channel, are each subtracted by operator 13. If this is indicated in channel n, a signal, as the output data of operator 13, can be obtained from the below equation (7).

$$\text{output data} = \frac{1}{C_n} \int_0^{T_n} I_n dt \cdot G \quad (7)$$

As is made clear from equation (7), leakage currents $i_1$-$i_n$ and off-set voltage $V_{os}$ of amplifier U, as error factors, are removed from the output data, so that input signal currents $I_1$-$I_n$ representative of the object being examined, are accurately measured. Thus the output data represents substantially true input signal currents.

In FIG. 3, signals $e_1$-$e_n$ are stored in memory 12 and signals $e_1'$-$e_n'$, as error factors, are directly introduced to operator 13 by switching circuit 14, without permitting the signals to pass through memory 12. However, the present invention can also be practiced by storing signals $e_1'$-$e_n'$, as error factors in memory 12, and then reading them out of the memory. Otherwise, the operation of error correction, may be carried out in a digital computer.

As mentioned above, according to the apparatus in FIG. 3, the effects of leakage currents $i_1$-$i_n$ and off-set voltage Vos of amplifier U, can be removed, so that the strength of the input signal currents $I_1$-$I_n$, can be accurately measured. From the standpoint of the following considerations, however, an apparatus with a construction different from FIG. 3, can be considered and employed. For example, in the apparatus shown in FIG. 3, a pair of measurements, e.g. "a signal including an off-set", and only the "offset", is required. Accordingly, measuring time is longer in duration, and the response speed of the appratus is relatively low. Moreover, the change of the off-set is generally slow in terms of time, and it is not necessary to measure the off-set each time measurement of the input signal is made.

Figure 5:
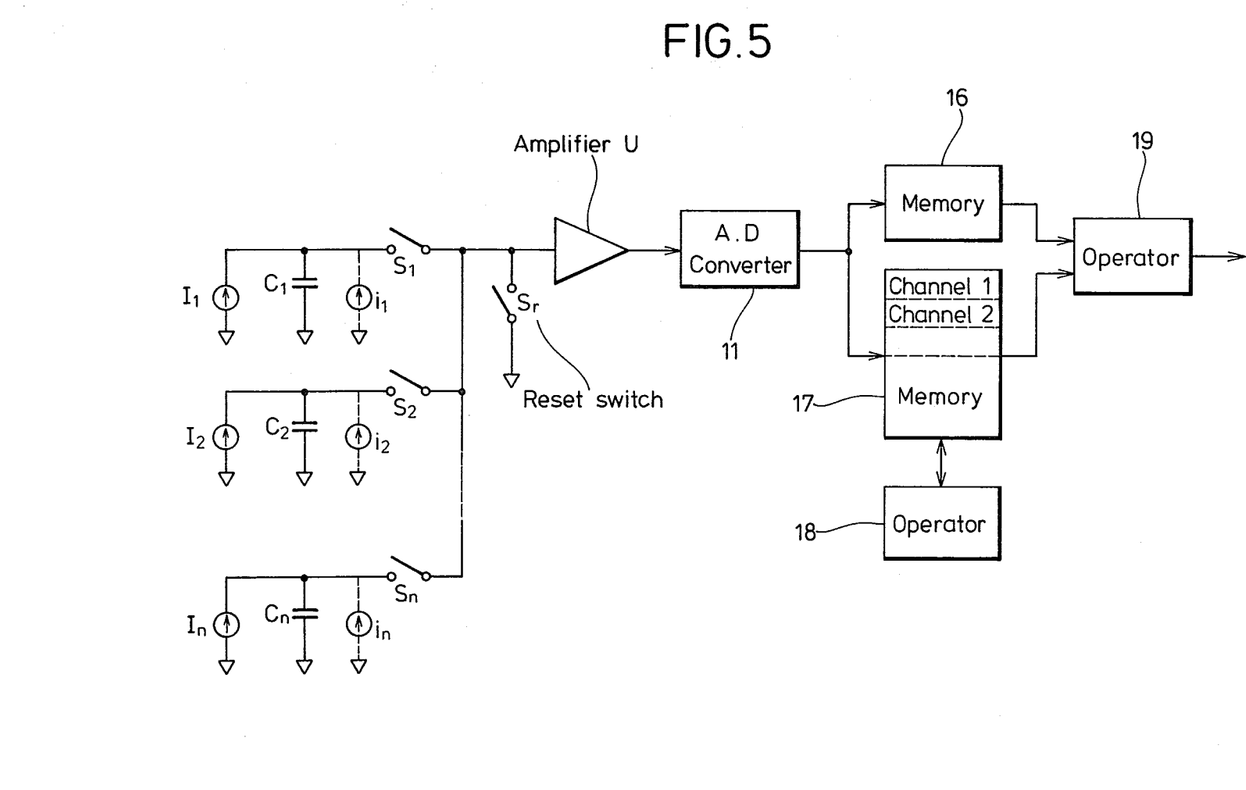
FIG. 5 depicts still another illustrative embodiment of the invention.
Figure 6:
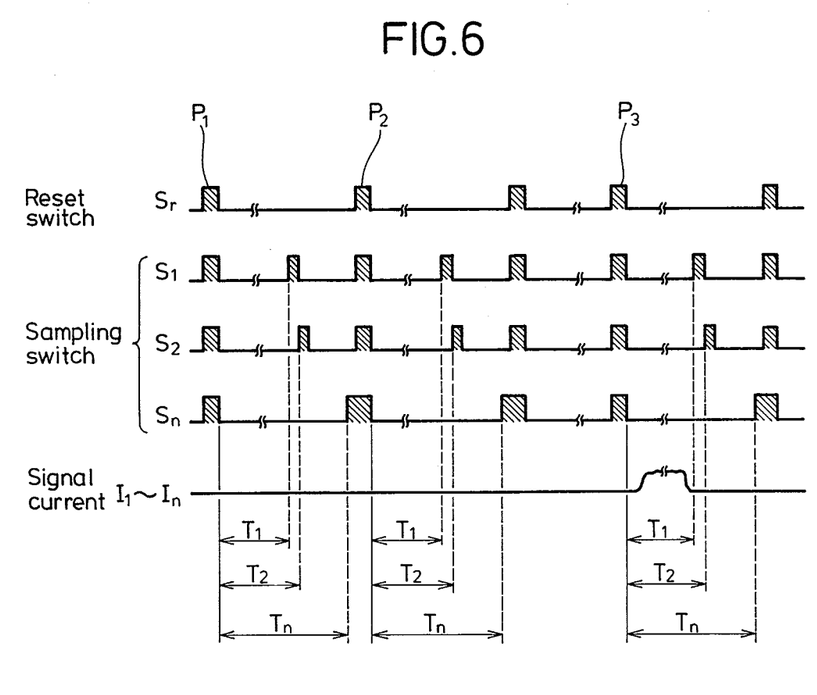
FIG. 6 is a time chart illustrating the operation of the embodiment of FIG. 5.

The embodiment of FIG. 5 overcomes the above consideration. FIG. 6 is a time chart illustrating the operation of the embodiment of FIG. 5. The operation of the embodiment of FIG. 5 may be summarized as follows. Only the off-set (a noise signal containing no signal current of the object being examined) is integrated during a period of time $T_i$, and the integrated value is stored in the memory. Next, a signal current containing the off-set is measured over a period of time Ti and the off-set value is stored in memory and then read out of the above measured value and subtracted to obtain a true input signal current. Then, each time a signal current, containing the offset, is measured over a period of time $T_i$, the above off-set value, that has been stored in the memory, is read out of the measured value and subtracted. The foregoing operation is then repeated for each channel and for each time measurement is made. In other words, the response speed of the apparatus is made higher by reducing the number of off-set measurements.

In FIG. 5, the description of input currents $I_1$-$I_n$, and elements $C_1$-$C_n$, $S_1$-$S_n$, Sr, U and 11, is omitted because they are similar to those described in FIGS. 1 and 3. Boxes 16 and 17 are memories for storing digital signals transmitted from AD converter 11. Boxes 18 and 19 are operating circuits for performing operations on signals applied thereto, such as subtraction, averaging, etc. Operator 18 functions to take out a plurality of data stored in memory 17 and to produce an average value. Operator 19 functions to take out data stored in memories 16 and 17 and to carry out addition and subtraction.

The capacitors $C_1$-$C_n$ are each connected between the input channels and circuit earth. The voltages of capacitors $C_1$-$C_n$ are led to amplifier U via sampling switches $S_1$-$S_n$ and to circuit earth via the contact point of reset switch Sr. The output of amplifier U is stored in each of memories 16 and 17 via the AD converter 11. The data stored in memories 16 and 17 are taken out to operator 19 when necessary, for predetermined computing purposes, so that data representing input signal currents $I_1$-$I_n$ without any off-set, can be obtained from the output of operator 19. Currents $i_1$-$i_n$, which are added to capacitors $C_1$-$C_n$ in parallel, represent leakage currents.

The description of the apparatus depicted in FIG. 5 and its operation, are given with reference to FIG. 6. In FIG. 6, among the waveforms indicating operations of the switches, the respective switch is assumed to be ON or OFF during the time the corresponding waveform is at a "high" or "low" level.

There are two conditions are stages of operation. First, error factors are determined, without application of input signal currents, averaged and stored; and, second, the input signal is applied and it together with the error factors, are measured, stored, and acted upon to remove the error factors, and thus produce an output signal representative of the true input signal.

DETERMINING ERROR FACTORS

During the period before input signal currents $I_1-I_n$ are applied, the off-set portion in each channel is first measured as follows.

(1) As shown in FIG. 6, when reset switch Sr is turned ON at time $P_1$, each of the sampling switches $S_1-S_n$ is concurrently turned ON. Accordingly, the charges in capacitors $C_1-C_n$, are discharged, and the voltages of the respective capacitors becomes zero.

(2) Subsequently, switches Sr and $S_1-S_n$ are all turned OFF and current based on the off-set is allowed to flow into each of capacitors $C_1-C_n$ and integrated therein.

(3) The sampling switch $S_1$ is first turned ON at time $T_1$ after capacitors $C_1-C_n$ have been discharged. The voltage of capacitor $C_1$ is read out and stored in memory 17 via amplifier U and AD converter 11.

(4) Then, sampling switch $S_2$ is turned ON at time $T_2$ after capacitors $C_1-C_n$ have been discharged. The voltage of capacitor $C_2$ is read out and stored in memory 17 via the same course as that in step (3).

(5) Then, the voltages of capacitors $C_3-C_n$ are all stored in memory 17 through the same operation as above.

(6) Each of sampling switches $S_1-S_n$ are all turned ON at the same time as reset switch Sr is again turned ON at $P_2$ and the voltages of capacitors $C_1-C_n$ becomes zero.

(7) The operations of steps (1)-(5) are repeated so that the data of the off-set in each channel, are again stored in memory 17, one after another.

(8) Repeating the above operation steps causes the off-set data in each channel to be stored in memory 17, with the data being collected during the predetermined period of time ($T_1$, $T_2$ ... $T_n$) on a per channel basis, after capacitors $C_1-C_n$ have been discharged.

(9) The data stored in memory 17, are taken out by channels, by operator 18, and an average value of off-set for each channel is calculated by operator 18, and then stored again in memory 17. For example, only data obtained from capacitor $C_1$ is used to produce an average value and the average value of the off-set factor in channel 1 is again stored in memory 17.

(10) The average value of the off-set factor in each channel is computed through the same operation and stored in memory 17.

In the present invention, the average value of the off-set portion in each channel during the period before the input signal currents $I_1-I_n$ have been applied, is computed and stored in the memory 17.

DETERMINING TRUE INPUT SIGNAL BY SUBTRACTING OUT THE AVERAGED ERROR FACTORS

The input signal currents $I_1-I_n$ are then measured as follows:

(11) As shown in FIG. 6, each of sampling switches $S_1-S_n$ is turned ON concurrently when reset switch Sr is turned ON at time $P_3$ and capacitors $C_1-C_n$ are discharged. That is the capacitors are cleared and ready for the measuring steps.

(12) Subsequently, as shown in FIG. 6, each of the input current signals $I_1-I_n$ flows into each of capacitors $C_1-C_n$ in each channel and is converted into a respective voltage.

(13) Switch $S_1$ is turned ON at time $T_1$ after capacitors $C_1-C_n$ have been discharged and the voltage data of capacitor $C_1$ are read out and stored in memory 16 via amplifier U and AD converter 11.

(14) Next, sampling switch $S_2$ is turned ON at time $T_2$ later and the voltage of capacitor $C_2$ is read out. The value obtained is stored in memory 16 through the same route as that in step (13).

(15) By the same operations as those in steps (13) and (14), the voltages of capacitors $C_3-C_n$ are all stored in memory 16.

(16) The measured data in each channel stored in memory 16 and the off-set portion in each channel previously stored in memory 17 are taken into operator 19 for operation whereby a true signal current from which the off-set portion has been removed can be obtained. That is, operator 19 will retrieve data for each channel, from memory 16, representing the input signal and circuit error factors, such as off-set, and from memory 17, representing the averaged error factors, and operate on such signals to substract the error factors from the stored combined signal comprising the input signal and error factor, and thus produce an output signal which is representative of the true input signal.

(17) Then, whenever input signal currents $I_1-I_n$ in the channel flow in, the correcting operation is repeated using the stored average error factors, including the off-set portion, which is stored in memory 17.

Although the above refers mainly to off-set factors, other error factors which exist in the circuit may be averaged out at the same time, since a signal obtained from the circuit when no input is applied, and then such signal is averaged and then subtracted from the signal resulting from the circuit when input signals are applied, that is a signal which comprises the input signal and the error factors. The same would apply for FIG. 3.

Operator 19 which operates to take out data stored in memories 16 and 17 and to carry out subtraction, may be a digital computer or the like. However, an analog operator may be used to practice the invention. In this case, it is necessary to provide a digital to analog converter in the stage prior to the operator 19 for converting the digital to analog signal.

In addition, although the above description has referred to two memories 16 and 17, separately installed, only one memory unit may be used, if the addressing thereof is separate.

According to the apparatus of FIG. 5, the off-set portion in each channel is measured and stored beforehand and the stored off-set portion is used for correcting computation each time the signal current is measured, so that the time required for measuring the current can be reduced to half, in comparison to the case of the apparatus, for example, shown in FIG. 3. As a result, a current measuring apparatus with high response speed is obtained. Furthermore, by taking into consideration noise and other error factors at the time of measuring the off-set data, such noise and other error factors are effectively reduced.

In all of the foregoing embodiments, each of the circuit elements per se are well known to the person skilled in the art, and hence are not described in detail, except for the detailed handling of the functions thereof. For example, the capacitors, switches, amplifiers, A.D. converters, memories, and operating units, are all well known, and their functions are outlined herein in detail so that any person skilled in the art can readily practice the invention upon consideration of the specification and drawings hereof.

The foregoing description is illustrative of the principles of the invention. Numerous extensions and modifications thereof would be apparent to the worker skilled in the art. All such extensions and modifications are to be considered to be within the spirit and scope of the invention.

What is claimed is:

1. A multichannel current measuring apparatus used in an X-ray computerized tomograph, for measuring the strength of an input signal current by charging a capacitor provided in each channel with a multichannel input signal current supplied by an X-ray detector and by reading out the corresponding voltage of the charged capacitor; said apparatus comprising in each channel, a capacitor, and a sampling switch; an amplifier having an input means and an output means; said sampling switch of each channel being connected between said input means of said amplifier and an associated capacitor in each channel; a reset switch connected to said input means of said amplifier; an analog-to-digital converter having input means and output means, said input means of said converter being connected to said output means of said amplifier; a memory for storing signals; an operating means for performing operations on signals received thereby, switch means for selectively supplying digital signals from said converter to said memory and to said operating means; and control means for controlling selected switching of said sampling switches, said reset switch and for controlling operation of said converter, said switching means, said memory and said operating means; whereby each of said capacitors is first cleared by concurrent switching ON and OFF of said plurality of sampling switches and said reset switch, and thereafter applying said input signals to said capacitors, and then subsequently sequentially turning ON and OFF of said sampling switches, to thereby supply combined signals representing said input signals and error factors to said amplifier for amplification, and then to said converter for conversion to digital form, and then to said memory for storage; and thereafter again clearing said capacitors of each channel by turning ON and OFF said plurality of sampling switches and said reset switch; and thereafter sequentially turning ON and OFF said sampling switches, thereby to supply signals from each capacitor representing error factors to said amplifier for amplification, and then to said converter for conversion to digital form, and switched by said switching means to said operating means; said operating means retrieving stored combined signals from said memory and subtracting therefrom said error factor signals, thereby to produce an output signal representative of substantially true input signals.

2. The apparatus of claim 1, wherein said control means causes said sampling switches to be turned ON at substantially the same time after being turned OFF in each operating cycle.

3. The apparatus of claim 1, wherein said switching means operates to cause signals representing said error factor to be directly transmitted to said operating means.

4. The apparatus of claim 1, wherein said switching means operates to cause signals representing said error factors to be transmitted to said memory and thereafter said operating means removes said error factor signals from said combined signal.

5. A multichannel current measuring apparatus used in a X-ray computerized tomograph, for measuring the strength of an input signal current by charging a capacitor provided in each channel with a multichannel input signal current supplied by an X-ray detector and by reading out the corresponding voltage of the charged capacitor; said apparatus comprising in each channel, a capacitor, and a sampling switch; an amplifier having input means and output means; said sampling switch of each channel being connected between said input means of said amplifier and an associated capacitor in each channel; a reset switch connected to said input means of said amplifier; an analog-to-digital converter having input means and output means, said output means of said amplifier being connected to said input means of said converter; a first memory and a second memory connected to said converter output; and first operating means connected to said first memory and to said second memory; and second operating means connected to said second memory; whereby each of said capacitors in each channel is first cleared by turning ON and OFF each of said sampling switches and said reset switch; and then, without application of any of said input signal currents, sequentially turning ON and OFF each of said sampling switches over at least two cycles, and measuring resulting voltages for each channel as applied to said amplifier, and then applying the amplified signals to said detector for conversion to digital form, and the applying digitalized signals to said second memory; said second operating means thereupon taking the signals from said second memory and averaging said signals from each channel, and subsequently storing the averaged error signal for each channel in said second memory; and whereby after clearing each capacitor by turning ON and OFF each of said sampling switches and said reset switch, said input signals are applied to each channel, and thereafter each of said sampling switches is sequentially turned ON and OFF thereby to cause combined signals comprising said input signals and error factors, to be supplied to said amplifier for amplification, and to said converter for conversion to digital form, and thereafter to said first memory, said first operating means thereupon taking said combined signal from said first memory and taking said averaged error signal from said second memory, and subtracting out said averaged error factors from said combined signal, thereby to produce an output signal representing a substantially accurate input signal for each channel.

6. The apparatus of claim 5, wherein said sampling switches and said reset switch are turned ON and OFF at substantially the same time in each cycle.

* * * * *